United States Patent

Madson, Jr. et al.

[11] Patent Number: 5,977,520
[45] Date of Patent: Nov. 2, 1999

[54] HEATING UNIT FOR THERAPEUTIC MOIST HEAT PACKS

[76] Inventors: Lawrence E. Madson, Jr., 61 Lambeth Dr., Upper St. Clair, Pa. 15241; Donald W. Stansbury, 4832 Scotch Pine Way, N. Ridgeville, Torain, Ohio 44039

[21] Appl. No.: 08/914,221

[22] Filed: Aug. 19, 1997

Related U.S. Application Data

[63] Continuation of application No. 08/511,465, Aug. 4, 1995, abandoned.

[51] Int. Cl.[6] .............................. F27D 11/00; H05B 3/02; A61F 7/08
[52] U.S. Cl. .......................... 219/429; 219/430; 219/436
[58] Field of Search .................................. 219/385–387, 219/429, 430, 432, 433, 436, 438, 439, 521

[56] References Cited

U.S. PATENT DOCUMENTS

| | | | |
|---|---|---|---|
| 1,659,719 | 2/1928 | Blake | 219/385 |
| 2,002,380 | 5/1935 | Wernicke et al. | 219/385 |
| 2,576,874 | 11/1951 | Acton | 219/387 |
| 2,577,870 | 12/1951 | Aston | 219/387 |
| 3,501,619 | 3/1970 | Buiting et al. | 219/386 |
| 3,881,090 | 4/1975 | Scott | 219/433 |
| 3,908,111 | 9/1975 | Bois et al. | 219/442 |
| 4,063,068 | 12/1977 | Johnson et al. | 219/386 |
| 4,198,559 | 4/1980 | Walter et al. | 219/387 |
| 4,215,267 | 7/1980 | Kaebitzsch | 219/439 |
| 4,234,783 | 11/1980 | Aoshima | 219/441 |
| 4,241,288 | 12/1980 | Aoshima et al. | 219/441 |
| 4,419,568 | 12/1983 | Van Overloop | 219/386 |
| 4,495,402 | 1/1985 | Burdick et al. | 219/521 |
| 4,857,708 | 8/1989 | Demars | 219/385 |
| 5,497,883 | 3/1996 | Monetti | 219/387 |

OTHER PUBLICATIONS

J.A. Preston Corporation, 12 and 4 Pack Midland Tropic Heater Unit. Date Unknown.
Chattanooga Corporation, Instructions for the Use and Operation of the Hydrocollator M–2 Master Heating Unit. Dec. 1990.
Forma–Splint Thermal Bath. Date Unknown.

*Primary Examiner*—Joseph Pelham
*Attorney, Agent, or Firm*—Sixbey, Friedman, Leedom & Ferguson; Daniel W. Sixbey

[57] ABSTRACT

A moist heat unit for applying heat to therapeutic moist heat packs includes a stainless steel tank for receiving water and the heat packs. The stainless steel tank is mounted in an insulating jacket having a stainless steel liner and a heat insulating outer cover, and the tank is mounted to create a continuous space between the tank and the stainless steel liner of the insulating jacket. A silastic, silicone rubber electric resistance heating assembly is bonded externally to the bottom of the stainless steel tank and is designed to provide wattage within a range of from 10 to 15 watts per square inch. The tank is closed by an insulated cover having an inner lining of stainless steel.

14 Claims, 1 Drawing Sheet

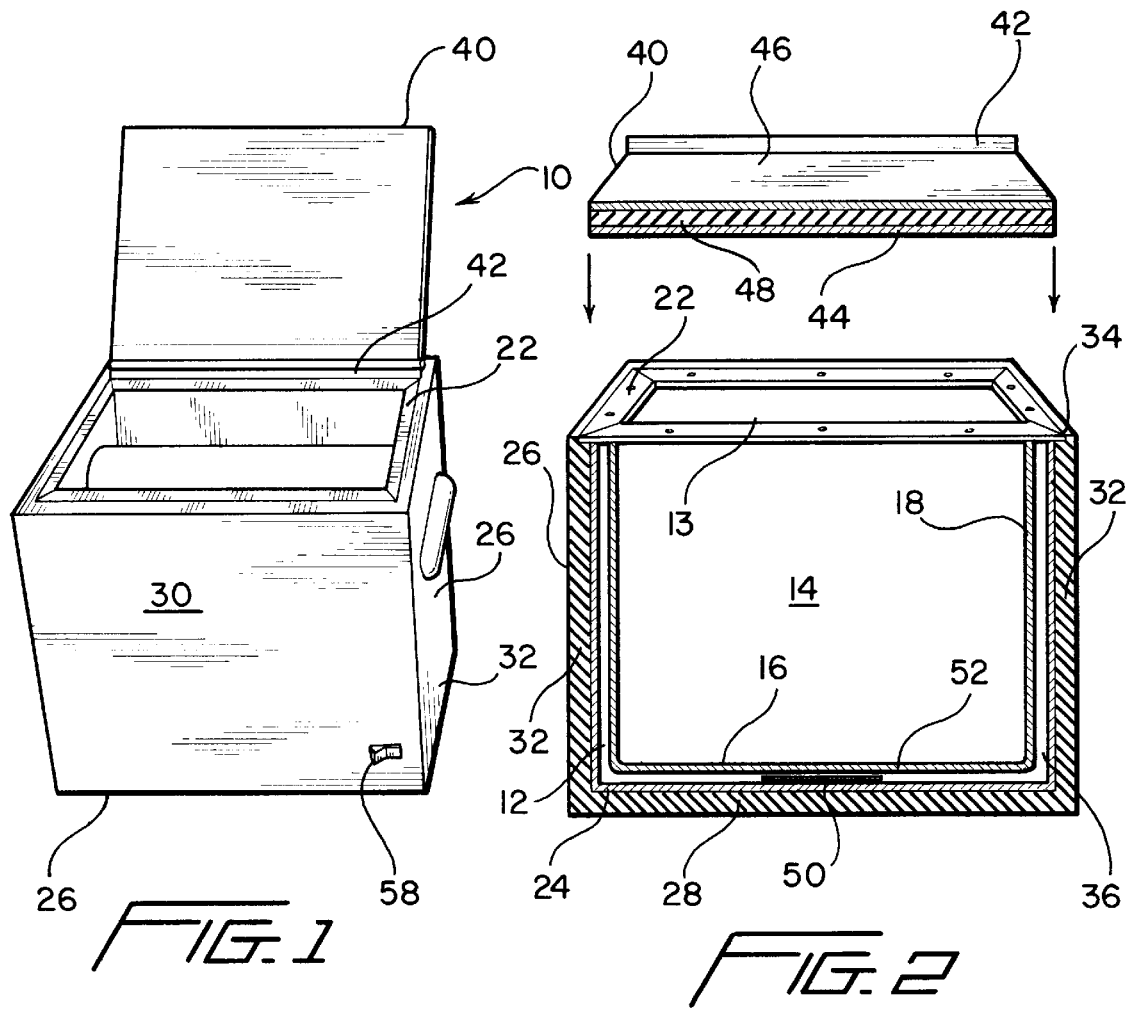
FIG. 1
FIG. 2
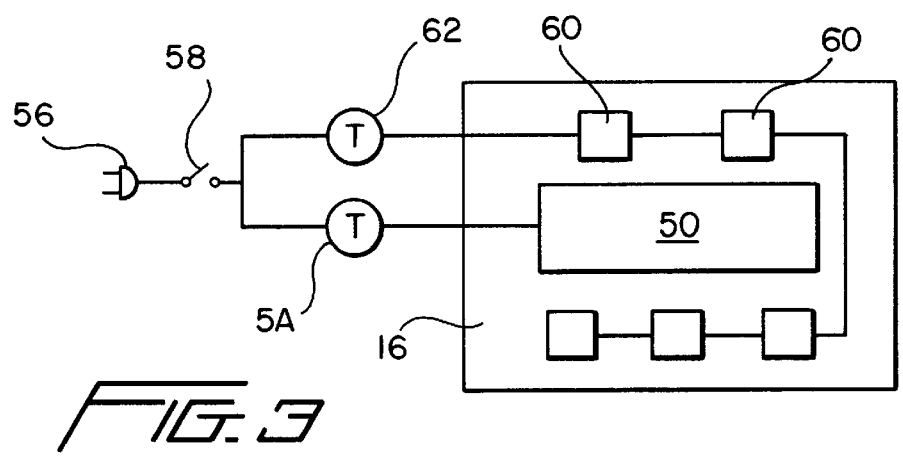
FIG. 3

HEATING UNIT FOR THERAPEUTIC MOIST HEAT PACKS

This application is a continuation of Ser. No. 08/511,465, filed Aug. 4, 1995, now abandoned,

TECHNICAL FIELD

The present invention relates generally to heating units for applying moist heat to moist heat packs used for therapeutic purposes, and more particularly to an improved moist heat unit which operates effectively with heating elements mounted on the outside of a working tank.

BACKGROUND

Moist heat packs for applying heat to localized body areas for therapeutic purposes, are normally constructed of heavy fabric, such as cotton canvas duck, and are filled with absorbent material which retains and provides moist heat for at least thirty minutes. In the past, moist heat packs have been heated with hot water in a stainless steel tank, since stainless steel may be effectively cleaned when the water is drained from the tank. However, stainless steel is a relatively poor heat conductor, and since the tanks are usually deep (11 inches–30 inches in depth), internally mounted electric dishwasher type calrod, electrical resistance heaters have been used to heat the volume of water within the tank. In a dishwasher with detergent and water circulation under pressure, calrod electrical resistance heaters are effective heating elements, but in a moist heat unit with standing water, dirt and sediment collects on the calrod electrical resistance heaters and they are difficult to access for cleaning. As dirt builds up, the calrod electrical resistance heater corrode, burn out and must be replaced. Also, if water is allowed to evaporate and the calrod electrical resistance heater is energized for a period of time in a dry tank, it is likely to fail.

Past attempts to use silicone rubber type electric resistance heating pads to the bottom of a stainless steel tank for a moist heat unit have failed, for at the minimum wattage needed to effectively penetrate the large area of stainless steel and heat and hold heat dissipating water at a temperature in the range of 150–180° F., the heaters delaminated from the tank. Even at wattages as low as 3½ watts per square inch, delamination occurred.

SUMMARY OF THE INVENTION

It is a primary object of the present invention to provide a novel and improved moist heat unit which includes a stainless steel tank and externally mounted electric heaters to heat water in the tank through the tank bottom wall.

Another object of the present invention is to provide a novel and improved moist heat unit which incorporates a stainless steel tank spaced within a heat insulating outer jacket, the open end of the tank being closed by a heat insulating lid with an inner cover layer of stainless steel. Silicone rubber electric heating pads are bonded to the bottom of the stainless steel tank in the space between the tank and the insulating jacket.

Yet another object of the present invention is to provide a novel and improved moist heat unit which employs a structural and electrical configuration of silicone rubber electric heaters bonded to the bottom of a stainless steel tank with a RTV sealant (100% silicone rubber) to provide 10–15 watts per square inch without delamination regardless of whether or not the tank contains water.

A still further object of this invention is to provide a novel and improved moist heat unit which combines an insulating jacket structure with a spaced stainless steel tank of a specific gauge and a silicone rubber heater structure configured to provide sufficient wattage to heat water within a tank of the specific gauge without delamination.

BRIEF DESCRIPTION OF THE DRAWINGS

FIG. 1 is a perspective view of the moist heat unit of the present invention;

FIG. 2 is an exploded sectional view of the moist heat unit of FIG. 1; and

FIG. 3 is a diagram of the electric heating system for the moist heat unit of FIG. 1.

DETAILED DESCRIPTION

The moist heat unit 10 of the present invention includes a stainless steel tank 12 having an access opening 13 at the uppermost extremity thereof leading to a chamber 14 which is defined by the tank bottom wall 16 and tank sidewalls 18. A laterally projecting flange 22 is provided at the uppermost extremity of the tank side walls and extends completely around the access opening 13.

The tank 12 fits into a central chamber 24 in an insulating casing 26 of a low, heat conductive material such as plastic. The casing may be formed of an inner layer of metal coated with a thick outer layer of heat insulating plastic material such as epoxy. The tank is held in place in spaced relationship to the bottom wall 28, the sidewalls 30 and the endwalls 32 of the insulating casing by the flange 22 which is fastened and sealed to the top edges 34 of the casing sidewalls 30 and endwalls 32 respectively. The tank is dimensioned so that it is spaced on all sides within a range of at least one half an inch to one inch from the insulating casing. This space is preferably maintained as an insulating, continuous air space 36, but it may be filled with a thermal insulating material.

Once the tank 12 is mounted in place within the insulating casing 26, a hinged insulating lid 40 is secured to the casing by means of a hinge 42. The insulating lid is dimensioned to rest on the flange 22 and, in the closed position, to close the access opening 13. This insulating lid is formed by an inner sheet of stainless steel 44, an outer sheet of stainless steel or a suitable plastic material 46, and an intervening layer of heat insulating material 48.

Before the stainless steel tank 12 is mounted within the insulating casing 26, one or more silastic (silicone rubber) heating units 50 are secured to the bottom wall 16 externally of the chamber 14 to provide heating through the bottom wall. Since stainless steel is a relatively poor heat conductor, the combined use of a tank formed of stainless steel within a range of from 16 to 22 gauge steel, external bottom heating, an insulated outside casing with a stainless steel inner surface spaced from the tank 12 and an insulated lid with a stainless steel inner surface, results in a moist heat unit 10 which operates effectively with little heat loss. However, to achieve this effective operation, it is necessary to drive heat through the stainless steel bottom wall 16 to rapidly heat water within the chamber 14 and to then maintain this water at an operating temperature of about 165 degrees F. With water in the stainless steel tank operating as a heat sink, there would be less need to closely control the watts per square inch which the heaters 50 apply to the bottom wall 16 of the tank 12 to maintain a low range of watts per square inch. In use, however, the tank may become short of water or actually be permitted to become dry, and consequently it is important to design a heating system which will not damage the unit if the tank becomes dry during use. If the wattage per square inch applied to the tank bottom wall is not within a controlled range, the silicone heaters 50 will rapidly delaminate from the tank bottom wall when the tank becomes low on water or dry, but the wattage range must be sufficient to rapidly heat the water within the tank.

Referring to FIG. 3, silastic silicone rubber, electric resistance heaters capable of applying wattage within a range of from 10 to 15 watts per square inch are bonded to the bottom wall 16 of the tank 12. When combined with the stainless steel tank, insulated hinged lid and insulating casing combination, silastic, silicone rubber heaters operative in this wattage range will rapidly and effectively heat water within the tank, and, when bonded in the manner to be described, will not delaminate when the tank runs dry. Silastic heater pads (Part Nos. A3200-385, A3200-407, A3100-1838, and A3100-1642) manufactured by Elmwood Sensors of Pawtucket Rhode Island and/or silastic, silicone rubber heater pads designated KSOT2 by Underwriters Laboratories operate effectively as the heaters 50 and 60, and these heater pads are bonded to the tank using a 100% silicone rubber adhesive 52 such as #732 clear, multiple purpose silastic, silicone rubber sealant manufactured by Dow Corning.

With reference to FIGS. 2 and 3, a 1000 watt silastic silicone rubber heater 50 is attached to the stainless steel tank bottom wall 16 by silicone rubber adhesive 52. For smaller moist heat units, this 1000 watt heater pad will provide wattage within the desired range of 10–15 watts per square inch so that the heater pad will not delaminate from the bottom wall 16 if the tank 12 becomes dry. The heater 50 is attached to a control thermostat 54 which is mounted inside the tank 16 to maintain the water in the tank at the desired operating temperature. This thermostat is connected to a power plug 56 for the moist heat unit by an on-off switch 58.

For larger moist heat units, small auxiliary silastic, silicone rubber heater pads 60 are bonded to the tank bottom 16. These auxiliary heaters may be 60 watt heaters connected in series to provide wattage within the range of 10–15 watts per square inch to the tank bottom wall. In FIG. 3, five 60 watt auxiliary heaters are connected in series to provide, with the heater 50, a total of 1300 watts. Obviously, the number of auxiliary heaters used will be determined by the area of the bottom wall 16 and the number and wattage of the heaters required to apply 10–15 watts per square inch to the tank bottom wall.

The auxiliary heaters 60 are connected to a second thermostat 62 which senses the temperature of the water in the tank 12. Ideally, this second thermostat is set at a lower control temperature than is the thermostat 54, so that the auxiliary heaters aid the main heater 50 during warm up, but cut off just below the operating temperature of the unit. For example, if the thermostat 54 is set to maintain an operating temperature of 165 degrees F., the thermostat 62 may be set to deenergize the auxiliary heaters when the water in the tank 12 reaches a temperature of 145 degrees F., and the main heater 50 will then be capable of raising the water temperature to operating temperature and maintaining the operating temperature.

The unique structure of the moist heat unit 10 wherein a stainless steel inner tank faces the stainless steel inner lining of the insulating casing 26 across a continuous space having a width within the range of one half to one inch coupled with the insulated lid 40 lined with an inwardly facing stainless steel sheet, facilitates the rapid and effective heating of water within the tank by an external silastic heater system bonded externally to the tank bottom and designed to provide wattage limited to 10–15 watts per square inch. The continuous space containing the silastic heaters is completely lined with stainless steel and results in sufficient heat being applied to the tank 12 without requiring a wattage which will cause heater delamination if the tank water level is low.

We claim:

1. A moist heat unit for heating water in which therapeutic moist heat packs are immersed to a temperature within a range of 150° F. to 180° F. and maintaining water at such temperature comprising:

a stainless steel tank for receiving water having interconnected tank sidewalls defining an internal tank chamber with an open end, a substantially flat tank bottom wall extending between said tank sidewalls across said tank chamber in spaced relation to said open end, said tank sidewalls and bottom wall being formed of stainless steel within a range of from 16 to 22 gauge and being dimensioned to form an internal tank chamber having a depth from said open end to said tank bottom wall within a range of from 11 to 30 inches, a heat insulating jacket surrounding said stainless steel tank having interconnected jacket sidewalls defining an internal jacket chamber with an open end, a jacket bottom wall extending between said jacket sidewalls across said jacket chamber in spaced relation to the open end of said jacket chamber, said jacket sidewalls and bottom wall being formed of a stainless steel inner layer dimensioned to be spaced from the bottom wall and the sidewalls of said stainless steel tank and an outer layer of insulating material bonded to said stainless steel inner layer, mounting means mounting and securing said stainless steel tank in said jacket chamber with the open end of said tank chamber adjacent to the open end of said jacket chamber, said mounting means mounting said stainless steel tank relative to the stainless steel layer of said heat insulating jacket to provide a continuous, stainless steel lined space between said tank sidewalls and bottom wall and said insulating jacket, a lid of heat insulating material mounted to close the open end of said tank chamber, and heating means for heating water in said tank by directly providing heat only to said tank bottom wall, said heating means including one or more silicone rubber electric resistance heaters bonded directly to said stainless steel tank bottom wall by a 100% silicone rubber adhesive and housed in the space between said tank bottom wall and the stainless steel layer of said jacket bottom wall, said one or more silicone rubber electric resistance heaters having a total operative wattage in relation to the area of the tank bottom wall sufficient to provide no more than a maximum wattage within a range of from ten to fifteen watts per square inch to said tank bottom wall to prevent delamination of the silicone rubber resistance heater or heaters from the tank bottom wall when the tank is devoid of water and to heat and maintain water in the tank to and within a range of 150° F. to 180° F.

2. The moist heat unit of claim 1 wherein said mounting means includes an outwardly extending flange on said stainless steel tank extending stainless steel annularly around the open end of said internal tank chamber, said flange being dimensioned to extend across the space between said tank and insulating jacket sidewalls and fastening means to secure said flange to said jacket sidewalls.

3. The moist heat unit of claim 1 wherein said lid of heat insulating material is formed of an inner layer of stainless steel and an outer layer of heat insulating material.

4. The moist heat unit of claim 3 wherein said stainless steel tank and heat insulating jacket are dimensioned to provide a continuous airspace within a range of from one half inch to one inch between said tank and the stainless steel layer of said insulating jacket.

5. The moist heat unit of claim 4 wherein the outer layer of said heat insulating jacket is formed of a heat insulating plastic bonded to said stainless steel inner layer, said lid including an outer layer of heat insulating material formed of heat insulating plastic and an inner layer of stainless steel.

6. The moist heat unit of claim 5 wherein said heat insulating plastic is epoxy.

7. The moist heat unit of claim 5 wherein said one or more silicone rubber electric resistance heaters includes a first silicone rubber electric resistance heater directly bonded to said tank bottom wall with silicone rubber adhesive, a first control thermostat connected to said first silicone rubber electric resistance heater and mounted to sense the temperature of water received in said stainless steel tank, said first control thermostat operating to deenergize said first silicone rubber electric resistance heater when said water reaches a first temperature, and an auxiliary heater means including at least one auxiliary silicone rubber electric resistance heater directly bonded to said tank bottom wall with silicone rubber adhesive and a second control thermostat connected to said auxiliary heater means and mounted to sense the temperature of water in said stainless steel tank, said second control thermostat operating to deenergize said auxiliary heater means when said water reaches a second temperature which is lower than said first temperature.

8. The moist heat unit of claim 7 wherein said auxiliary heater means includes a plurality of auxiliary silicone rubber electric resistance heaters connected in series and directly bonded to said tank bottom wall, said auxiliary silicone rubber electric resistance heaters each providing a wattage lower than that provided by said first silicone rubber electric resistance heater.

9. A method for forming a moist heat unit for heating therapeutic moist heat packs and water to a temperature within a range of from 150° F. to 180° F. in a stainless steel tank having a depth of from 11 to 30 inches solely by means of one or more silicone rubber electric resistance heaters bonded externally to the bottom of the stainless steel tank without delamination of the silicone rubber electric resistance heaters when the heaters are energized and the tank is dry which includes:

providing a stainless steel tank having interconnected tank sidewalls defining an internal tank chamber with an open end and a tank bottom wall extending between said tank sidewalls across said tank chamber in spaced relation to the open end to form a tank chamber having a depth within the range of from 11 to 30 inches, bonding one or more silicone rubber electric resistance heaters directly to the stainless steel tank bottom wall externally of said tank chamber which have a limited, maximum total operative wattage range in relation to the area of the tank bottom wall which is limited to providing a maximum wattage within a range of from 10 to 15 watts per square inch to the tank bottom wall, providing a heat insulating jacket having interconnected jacket sidewalls defining an internal, open ended, jacket chamber dimensioned to receive and surround said stainless steel tank with a jacket bottom wall extending between the jacket sidewalls across the jacket chamber in spaced relationship to the open end of the jacket chamber, the jacket sidewalls and bottom wall being formed of a stainless steel inner layer dimensioned to be spaced from the bottom wall and sidewalls of the stainless steel tank when the stainless steel tank is received in said jacket chamber and an outer layer of heat insulating material secured to said stainless steel inner layer, mounting the stainless steel tank in the jacket chamber with the open end of the tank chamber adjacent to the open end of the jacket chamber and with the stainless steel tank side and bottom walls spaced from the stainless steel inner layer of said heat insulating jacket to provide a continuous stainless steel lined space between said tank sidewalls and bottom wall and said insulating jacket which receives said one or more silicone rubber electrical resistance heaters, and mounting a lid of heat insulating material to selectively open or close the open end of said tank chamber.

10. The method of claim 9 which includes bonding said one or more silicone rubber electric resistance heaters to said tank bottom wall with a 100% silicone rubber adhesive.

11. The method of claim 9 which includes providing a lid of heat insulating material which closes the open ends of said tank and jacket chambers and includes an inner layer of stainless steel.

12. The method of claim 9 which includes providing a stainless steel tank having tank sidewalls and a bottom wall formed of stainless steel within a range of from 16–22 gauge.

13. The method of claim 12 which includes providing a stainless steel tank and heat insulating jacket dimensioned to space said tank sidewalls and bottom wall from the stainless steel inner layer of said heat insulating jacket for a distance within a range of from ½ to 1 inch when said stainless steel tank is mounted in said jacket chamber.

14. The method of claim 13 which includes bonding said one or more silicone rubber electric resistance heaters to said tank bottom wall with an 100% silicone rubber adhesive.

* * * * *